US012611185B2

(12) United States Patent
Takahashi

(10) Patent No.: US 12,611,185 B2
(45) Date of Patent: Apr. 28, 2026

(54) ULTRASOUND RECEPTION APPARATUS APPLYING ADAPTIVE RECEPTION BEAMFORMING TO SYNTHESIS PROCESSING AND ULTRASOUND RECEPTION METHOD APPLYING ADAPTIVE RECEPTION BEAMFORMING TO SYNTHESIS PROCESSING

(71) Applicant: CANON MEDICAL SYSTEMS CORPORATION, Otawara (JP)

(72) Inventor: Hiroki Takahashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 18/501,278

(22) Filed: Nov. 3, 2023

(65) Prior Publication Data

US 2024/0148365 A1 May 9, 2024

(30) Foreign Application Priority Data

Nov. 8, 2022 (JP) ................................. 2022-179067

(51) Int. Cl.
*A61B 8/00* (2006.01)

(52) U.S. Cl.
CPC .......... *A61B 8/5207* (2013.01); *A61B 8/4461* (2013.01); *A61B 8/5269* (2013.01)

(58) Field of Classification Search
CPC ........................ G01S 7/52038; G01S 15/8963
See application file for complete search history.

(56) References Cited

U.S. PATENT DOCUMENTS 6,363,033 B1* 3/2002 Cole ................... G10K 11/345
367/138
2014/0058262 A1* 2/2014 Yoda ................... G01S 7/52047
600/407
(Continued)

FOREIGN PATENT DOCUMENTS

JP 2018-187014 A 11/2018

OTHER PUBLICATIONS

Extended European Search Report Issued Mar. 21, 2024 in European Application 23208094.5, 11 pages.
(Continued)

*Primary Examiner* — Nyrobi Celestine
(74) *Attorney, Agent, or Firm* — Oblon, McClelland, Maier & Neustadt, L.L.P.

(57) ABSTRACT

An ultrasound reception apparatus according to one embodiment includes signal processing circuitry. The signal processing circuitry is configured to: acquire first reflected wave data for each channel, the first reflected wave data being generated by chronologically transmitting and receiving ultrasound waves in different transmission directions; perform phasing processing corresponding to a transmission path for each channel with respect to each piece of the first reflected wave data, and generates second reflected wave data; perform addition processing with respect to a plurality of transmission directions for each channel by using the second reflected wave data, and generates third reflected wave data subjected to transmit aperture synthesis; and perform adaptive reception beamforming on the third reflected wave data.

9 Claims, 11 Drawing Sheets

(56) References Cited

U.S. PATENT DOCUMENTS

| | | | |
|---|---|---|---|
| 2014/0240482 A1* | 8/2014 | Ikeda | H04N 23/632 |
| | | | 348/77 |
| 2015/0071030 A1* | 3/2015 | Hayashi | G01S 7/52023 |
| | | | 367/7 |
| 2015/0351720 A1* | 12/2015 | Ikeda | A61B 8/5207 |
| | | | 600/447 |
| 2017/0150947 A1 | 6/2017 | Yoshizawa et al. | |
| 2017/0224310 A1* | 8/2017 | Fuse | A61B 8/54 |
| 2018/0149734 A1* | 5/2018 | Zhai | G01S 15/8997 |
| 2019/0072671 A1* | 3/2019 | Nikolov | G01S 15/8993 |
| 2019/0209133 A1* | 7/2019 | Takahashi | A61B 8/5207 |
| 2021/0386404 A1* | 12/2021 | Walker | G01S 7/52046 |
| 2022/0155439 A1* | 5/2022 | Rindal | G01S 15/8915 |

OTHER PUBLICATIONS

Wang, Shun-Li et al., "MVDR-Based Coherence Weighting for High-Frame-Rate Adaptive Imaging", IEEE Transactions on Ultrasonics, Ferroelectrics, and Frequency Control, vol. 56, No. 10, 2009, pp. 2097-2110, XP011279147.

Wang, Yu-Hsin et al., "SNR-Dependent Coherence Weighting for Minimum Variance Beamforming", IEEE International Ultrasonics Symposium Proceedings, 2011, pp. 2452-2455, XP032230894.

* cited by examiner

DELAY                 ADDITION

ULTRASOUND RECEPTION APPARATUS APPLYING ADAPTIVE RECEPTION BEAMFORMING TO SYNTHESIS PROCESSING AND ULTRASOUND RECEPTION METHOD APPLYING ADAPTIVE RECEPTION BEAMFORMING TO SYNTHESIS PROCESSING

CROSS-REFERENCE TO RELATED APPLICATIONS

This application is based upon and claims the benefit of priority from Japanese Patent Application No. 2022-179067, filed on Nov. 8, 2022; the entire contents of which are incorporated herein by reference.

FIELD

Embodiments described herein relate generally to an ultrasound reception apparatus and an ultrasound reception method.

BACKGROUND

Conventionally, an ultrasound diagnostic apparatus that implements transmit aperture synthesis for generating an image with high uniformity and less noise is known. Further, an ultrasound diagnostic apparatus that performs adaptive reception beamforming for improving resolution of an image is known.

Furthermore, by applying the adaptive reception beamforming to the transmit aperture synthesis, it is expected to further improve image quality.

However, the adaptive reception beamforming increases a processing load, and therefore, it is not realistic to apply the adaptive reception beamforming to the transmit aperture synthesis.

DETAILED DESCRIPTION

An ultrasound reception apparatus according to one embodiment includes an acquisition unit, a phasing addition processing unit, a transmit aperture synthesis unit, and an adaptive reception beamforming unit. The acquisition unit acquires first reflected wave data for each channel, where the first reflected wave data is generated by chronologically transmitting and receiving ultrasound waves in different transmission directions. The phasing addition processing unit performs phasing addition processing corresponding to a transmission path for each channel with respect to each piece of the first reflected wave data, and generates second reflected wave data. The transmit aperture synthesis unit performs addition processing with respect to a plurality of transmission directions by using the second reflected wave data for each channel, and generates third reflected wave data. The adaptive reception beamforming unit performs adaptive reception beamforming on the third reflected wave data.

Embodiments of an ultrasound reception apparatus and an ultrasound reception method will be described below with reference to the drawings. In the embodiments below, components denoted by the same reference symbols perform the same operation, and repeated explanation will be omitted appropriately.

Figure 1:
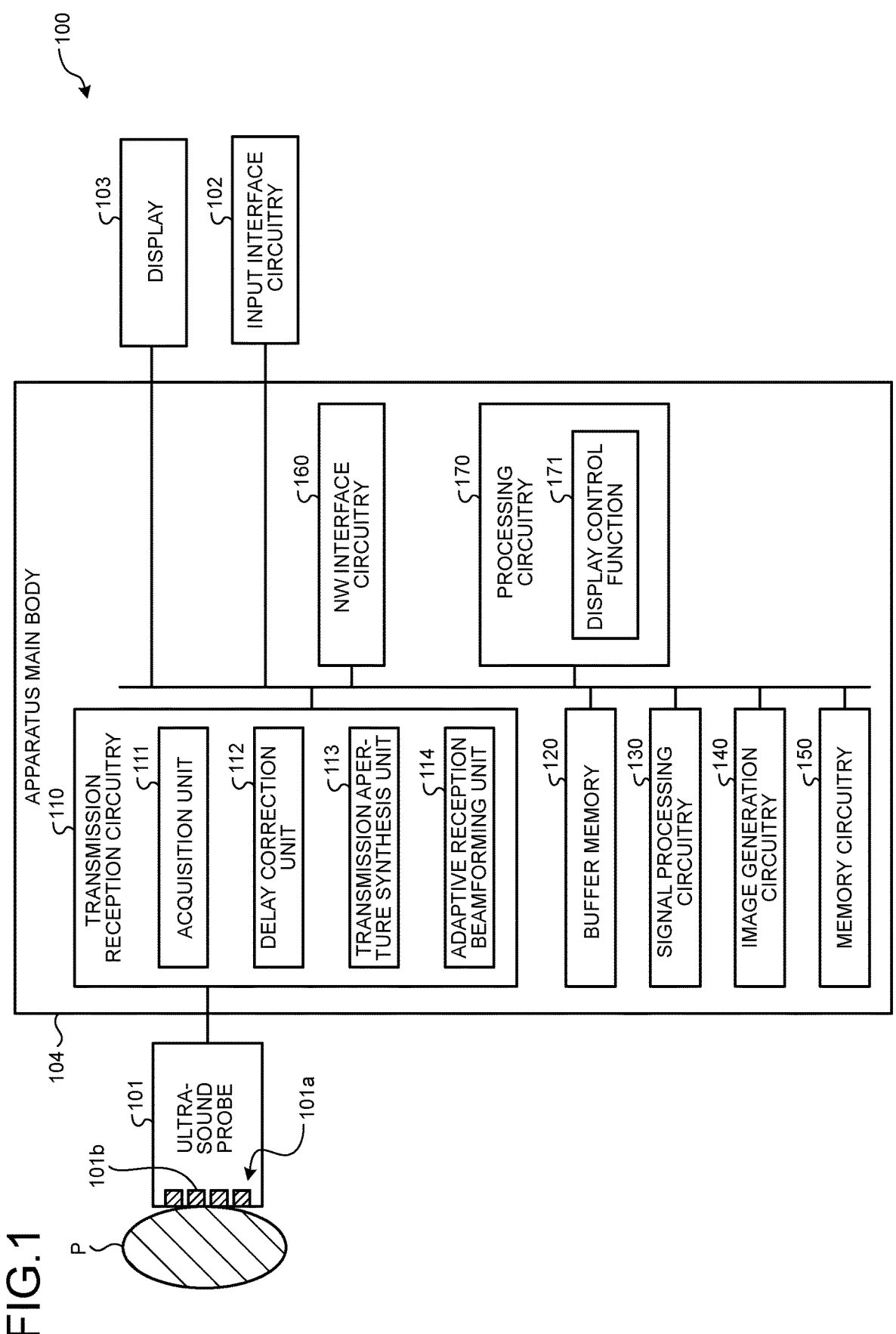
FIG. 1 is a block diagram illustrating an example of a configuration of an ultrasound diagnostic apparatus according to the present embodiment.

FIG. 1 is a block diagram illustrating an example of a configuration of an ultrasound diagnostic apparatus 100 according to the present embodiment. As illustrated in FIG. 1, the ultrasound diagnostic apparatus 100 includes an ultrasound probe 101, an input interface circuitry 102, a display 103, and an apparatus main body 104. The ultrasound probe 101, the input interface circuitry 102, and the display 103 are communicably connected to the apparatus main body 104.

The ultrasound probe 101 includes an array unit 101a in which a plurality of piezoelectric elements 101b are arrayed. The array unit 101a generates an ultrasound wave based on a driving signal that is supplied from transmission reception circuitry 110 included in the apparatus main body 104. Further, the ultrasound probe 101 receives a reflected wave from a subject P and converts the reflected wave to an electrical signal. Meanwhile, the ultrasound probe 101 is detachably connected to the apparatus main body 104.

When the ultrasound wave is transmitted from the ultrasound probe 101 to the subject P, the transmitted ultrasound wave is sequentially reflected by a discontinuous surface of acoustic impedance in body tissue of the subject P, and is received, as a reflected wave signal, by the array unit 101a included in the ultrasound probe 101. Amplitude of the received reflected wave signal is dependent on an acoustic impedance difference at the discontinuous surface at which the ultrasound wave is reflected. A reflected wave signal that is obtained when a transmitted ultrasound pulse is reflected by a surface of moving blood flow, a heart wall, or the like is dependent on a velocity component of a moving body in an ultrasound wave transmission direction due to the Doppler effect, and is subjected to frequency shift.

Meanwhile, the form of the ultrasound probe 101 is not specifically limited, and an ultrasound probe in any form is applicable. For example, the ultrasound probe 101 may be a one-directional (1D) array probe that scans the subject P in a two-dimensional manner. Further, the ultrasound probe 101 may be a mechanical four-dimensional (4D) probe or a two-dimensional (2D) array probe that scans the subject P in a three-dimensional manner.

The input interface circuitry 102 receives input operation of various kinds of instruction and various kinds of information from an operator. Specifically, the input interface circuitry 102 converts the input operation that is received from the operator to an electrical signal, and outputs the electrical signal to processing circuitry 170 of the apparatus main body 104. For example, the input interface circuitry 102 is implemented by a trackball, a switch button, a mouse, a keyboard, a touch pad that performs input operation by touching on an operation surface, a touch screen in which a display screen and a touch pad are integrated, contactless input circuitry using an optical sensor, voice input circuitry, or the like. Meanwhile, the input interface circuitry 102 is not limited to those including a physical operating part, such as a mouse or a keyboard. For example, examples of the input interface circuitry 102 include electrical signal processing circuitry that receives an electrical signal corresponding to input operation from an external input apparatus that is arranged separately from the apparatus, and outputs the electrical signal to control circuitry.

The display 103 displays various kinds of information and images. Specifically, the display 103 converts information and image data transmitted from the processing circuitry 170 to an electrical signal for display, and outputs the electrical signal. For example, the display 103 is implemented by a liquid crystal monitor, a Cathode Ray Tube (CRT) monitor, a touch panel, or the like. Meanwhile, an output apparatus included in the ultrasound diagnostic apparatus 100 is not limited to the display 103, and may include, for example, a speaker. For example, the speaker outputs a predetermined sound, such as a beep sound, to notify an operator of a processing condition of the apparatus main body 104.

The apparatus main body 104 is an apparatus that generates an ultrasound image based on the reflected wave signal that is received by the ultrasound probe 101. For example, the apparatus main body 104 generates a two-dimensional ultrasound image based on two-dimensional reflected wave data that is received by the ultrasound probe 101. Further, the apparatus main body 104 generates a three-dimensional ultrasound image based on three-dimensional reflected wave data that is received by the ultrasound probe 101.

The apparatus main body 104 includes, as illustrated in FIG. 1, the transmission reception circuitry 110, a buffer memory 120, signal processing circuitry 130, image generation circuitry 140, memory circuitry 150, a network (NW) interface circuitry 160, and the processing circuitry 170. The transmission reception circuitry 110, the buffer memory 120, the signal processing circuitry 130, the image generation circuitry 140, the memory circuitry 150, the NW interface circuitry 160, and the processing circuitry 170 are communicably connected to one another.

The transmission reception circuitry 110 includes a pulse generator, a transmission delay unit, a pulsar, and the like, and supplies a driving signal to the ultrasound probe 101. The pulse generator repeatedly generates a rate pulse for forming a transmission ultrasound wave at a predetermined rate frequency. Further, the transmission delay unit gives a delay time for each of the piezoelectric elements 101*b*, which is needed to focus ultrasound waves generated by the ultrasound probe 101 in a beam and determine transmission directivity, to each rate pulse that is generated by the pulse generator. Further, the pulsar applies a driving signal (driving pulse) to the ultrasound probe 101 at a certain timing that is based on the rate pulse. That is, the transmission delay unit, by changing a delay time to be given to each rate pulse, arbitrarily adjusts the transmission direction of the ultrasound wave that is transmitted form a surface of the array unit 101*a*.

Furthermore, the transmission reception circuitry 110 includes a preamplifier, an Analog-to-Digital (A/D) converter, quadrature detection circuitry, and the like, performs various kinds of processing on the reflected wave signal that is received by the ultrasound probe 101, and generates reflected wave data.

The preamplifier performs gain adjustment (gain correction) by amplifying the reflected wave signal for each channel. The A/D converter performs A/D conversion on the reflected wave signal that is subjected to the gain correction, and converts the reflected wave signal that is subjected to the gain correction to a digital signal. The quadrature detection circuitry converts the reflected wave signal that is subjected to the A/D conversion to an In-phase signal (an I signal, where I represents In-phase) and a quadrature signal (a Q signal, where Q represents Quadrature-phase) in a baseband band.

The quadrature detection circuitry outputs the I signal and the Q signal as the reflected wave data. Hereinafter, the I signal and the Q signal may be collectively referred to as an IQ signal. Further, the IQ signal is digital data that is subjected to the A/D conversion, and therefore, may be referred to as IQ data.

The transmission reception circuitry 110 is implemented by semiconductor integrated circuitry, such as an Application Specific Integrated Circuit (ASIC) or a Field Programmable Gate Array (FPGA). Further, the transmission reception circuitry 110 includes an acquisition unit 111, a delay correction unit 112, a transmit aperture synthesis unit 113, and an adaptive reception beamforming unit 114.

The acquisition unit 111 acquires first reflected wave data that is reflected wave data indicating reflected waves that are detected by the piezoelectric elements 101*b* that are arranged in a plurality of arrays in the array unit 101*a*. More specifically, the array unit 101*a* transmits ultrasound waves in different directions at a plurality of timings. Further, the array unit 101*a* receives reflected waves that are obtained by reflection of the ultrasound waves that are transmitted in the different directions at the plurality of timings. That is, the acquisition unit 111 acquires the first reflected wave data that indicates a reflected wave for each channel, which is generated by chronologically transmitting and receiving the ultrasound waves in different transmission directions. Here, for each channel means, for example, for each of the piezoelectric elements 101*b*. However, for each channel is not limited to this example, and, for example, it may be possible to form a single channel by the plurality of piezoelectric elements 101*b*.

The delay correction unit 112 performs phasing addition processing corresponding to a transmission path for each channel with respect to each piece of the first reflected wave data, and generates second reflected wave data. The delay correction unit 112 is one example of a phasing addition processing unit. That is, the delay correction unit 112 adds, to the first reflected wave data, a delay that corresponds to a transmission path including a forward path until reflection of the ultrasound waves transmitted from the piezoelectric elements 101*b* and a backward path from the reflection of the ultrasound waves until arrival of the ultrasound waves to the piezoelectric elements 101*b*. The delay correction unit 112, by adding the delay to the first reflected wave data, generates the second reflected wave data that is reflected wave data of the reflected wave added with the delay.

The transmit aperture synthesis unit 113 performs addition processing in the plurality of transmission directions for each channel by using the second reflected wave data, and generates third reflected wave data subjected to transmit aperture synthesis. The transmit aperture synthesis is a process of improving uniformity of a sound field by synthesizing, for each channel, the reflected waves that are obtained by reflecting the ultrasound waves that are transmitted in different directions at a plurality of timings.

Here, the array unit 101a transmits the ultrasound waves in a plurality of different directions. Therefore, a plurality of reflected waves that are detected by the same piezoelectric element 101b are reflection of the ultrasound waves that are transmitted in the different directions at the plurality of timings. Therefore, the transmit aperture synthesis unit 113 is able to implement the transmit aperture synthesis by performing the addition processing for each channel, with respect to the plurality of transmission directions by using the second reflected wave data.

The adaptive reception beamforming unit 114 performs the adaptive reception beamforming on the third reflected wave data that is generated by the synthesis performed by the transmit aperture synthesis unit 113. The adaptive reception beamforming unit 114 performs the adaptive reception beamforming on the third reflected wave data, and generates fourth reflected wave data.

More specifically, the adaptive reception beamforming is a process of improving image quality by performing specific calculation in a process of adding a delay to the reflected wave received by each of the piezoelectric elements 101b or in a process of adding the reflected waves that are added with the delays. For example, the adaptive reception beamforming includes a Minimum Variance (MV) method of correcting amplitude or a phase of the received reflected wave and suppressing an unneeded component, a Delay Multiply and Sum (DMAS) method of multiplication to increase sensitivity of response to a delay lag, and the like.

That is, the adaptive reception beamforming unit 114 performs the adaptive reception beamforming of the MV system on the third reflected wave data. Alternatively, the adaptive reception beamforming unit 114 performs the adaptive reception beamforming of the DMAS system on the third reflected wave data. Further, the adaptive reception beamforming unit 114 stores the fourth reflected wave data, as the reflected wave data, in the buffer memory 120.

The buffer memory 120 is implemented by, for example, a semiconductor memory element, such as a Random Access Memory (RAM) or a flash memory. The buffer memory 120 stores therein the reflected wave data that is output from the transmission reception circuitry 110. Meanwhile, the buffer memory 120 may store therein temporary data, such as the first reflected wave data, the second reflected wave data, or the third reflected wave data.

The signal processing circuitry 130 acquires the reflected wave data that is stored in the buffer memory 120. Further, the signal processing circuitry 130 generates data (B-mode data) in which signal intensity is represented by intensity of luminance, by performing logarithmic amplification, envelope detection processing, or the like on the reflected wave data that is acquired from the buffer memory 120. Further, the signal processing circuitry 130 performs a frequency analysis on velocity information based on the reflected wave data that is acquired from the buffer memory 120, extracts a blood flow, tissue, or a contrast agent echo component due to the Doppler effect, and generates data (Doppler data) in which moving body information, such as velocity, variance, or power, is extracted at multiple points.

Furthermore, the signal processing circuitry 130 is able to perform processing on both of two-dimensional reflected wave data and three-dimensional reflected wave data. That is, the signal processing circuitry 130 generates two-dimensional B-mode data from the two-dimensional reflected wave data, and generates three-dimensional B-mode data from the three-dimensional reflected wave data. Moreover, the signal processing circuitry 130 generates two-dimensional Doppler data from the two-dimensional reflected wave data, and generates three-dimensional Doppler data from the three-dimensional reflected wave data.

The image generation circuitry 140 generates an ultrasound image from the data that is generated by the signal processing circuitry 130. For example, the image generation circuitry 140 generates a two-dimensional B-mode image in which the intensity of the reflected wave is represented by luminance, from the two-dimensional B-mode data that is generated by the signal processing circuitry 130.

Furthermore, for example, the image generation circuitry 140 generates a two-dimensional Doppler image in which blood flow information is visualized, from the two-dimensional Doppler data that is generated by the signal processing circuitry 130. The two-dimensional Doppler image is velocity image data that represents average velocity of the blood flow, variance image data that represents a variance value of the blood flow, power image data that represents power of the blood flow, or image data in which the velocity image data, the variance image data, and the power image data are combined. Moreover, the image generation circuitry 140 generates, as the Doppler image, a color Doppler image in which blood flow information, such as the average velocity, the variance value, or the power of the blood flow, is displayed in color, or a Doppler image in which a single piece of the blood flow information is displayed in grayscale.

Furthermore, for example, the image generation circuitry 140 may generate an M-mode image from chronological data of the B-mode data on a single scanning line that is generated by the signal processing circuitry 130. Moreover, the image generation circuitry 140 may generate a Doppler waveform by chronologically plotting velocity information on the blood flow or tissue, from the Doppler data that is generated by the signal processing circuitry 130.

Here, the image generation circuitry 140 generally converts (scan convert) a scanning line signal train of ultrasound wave scanning into a scanning line signal train of a video format represented by television or the like, and generates an ultrasound image to be displayed. Specifically, the image generation circuitry 140 performs coordinate transformation in accordance with an ultrasound wave scanning mode performed by the ultrasound probe 101, and generates the ultrasound image to be displayed. Furthermore, the image generation circuitry 140 performs, as various kinds of image processing in addition to the scan convert, image processing (smoothing processing) of re-generating a luminance average value image, image processing (edge enhancement processing) using a differential filter in the image, or the like by using a plurality of image frames subjected to the scan convert, for example. Moreover, the image generation circuitry 140 synthesizes character information on various parameters, a scale, a body mark, or the like with the ultrasound image data.

That is, the B-mode data and the Doppler data are data before being subjected to the scan convert processing, and the data generated by the image generation circuitry 140 is image data that is subjected to the scan convert processing and that is to be displayed. Hereinafter, the data before being subjected to the scan convert processing (the B-mode data and the Doppler data) may be referred to as "RAW data".

The image generation circuitry 140 generates a two-dimensional B-mode image and a two-dimensional Doppler image that are two-dimensional ultrasound images from two-dimensional B-mode data and two-dimensional Doppler data that are the RAW data. Furthermore, the image generation circuitry 140 may generate a superimposed image in which, for example, a color Doppler image is superimposed on the two-dimensional B-mode image.

The memory circuitry 150 stores therein various kinds of data. For example, the memory circuitry 150 stores therein a control program for transmitting and receiving ultrasound waves, for performing image processing and display processing, or the like, and various kinds of data, such as diagnosis information (for example, a patient ID, an opinion of a doctor, or the like), a diagnosis protocol, or various kinds of body marks. For example, the memory circuitry 150 is implemented by a semiconductor memory element, such as a Random Access Memory (RAM) or a flash memory, a hard disk drive (HDD), an optical disk, or the like.

Furthermore, the data that is stored in the memory circuitry 150 may be transferred to an external apparatus via the NW interface circuitry 160. Meanwhile, examples of the external apparatus include a personal computer (PC) and a tablet terminal that are used by a doctor who performs image diagnosis, an image storage apparatus for storing images, and a printer.

The NW interface circuitry 160 controls communication that is performed between the apparatus main body 104 and the external apparatus. Specifically, the NW interface circuitry 160 receives various kinds of information from the external apparatus, and outputs the received information to the processing circuitry 170. For example, the NW interface circuitry 160 is implemented by a network card, a network adapter, a Network Interface Controller (NIC), or the like.

The processing circuitry 170 controls entire processing performed by the ultrasound diagnostic apparatus 100. Specifically, the processing circuitry 170 controls processing performed by the transmission reception circuitry 110, the signal processing circuitry 130, and the image generation circuitry 140 based on various kinds of setting requests that are input by an operator via the input interface circuitry 102, or various kinds of control programs and various kinds of data that are read from the memory circuitry 150. Further, the processing circuitry 170 controls display of the ultrasound image.

Furthermore, the processing circuitry 170 implements a display control function 171. Here, for example, each of processing functions of the display control function 171 that is a constituent element of the processing circuitry 170 is stored in the memory circuitry 150 in the form of a computer executable program. The processing circuitry 170 is a processor. For example, the processing circuitry 170 reads programs from the memory circuitry 150, executes the programs, and implements functions corresponding to each of the programs. In other words, the processing circuitry 170 that has read each of the programs has each of the functions illustrated in the processing circuitry 170 in FIG. 1. Meanwhile, in FIG. 1, it is explained that the single processor implements the processing functions performed by the display control function 171, but it may be possible to construct the processing circuitry 170 by combining a plurality of independent processors, and cause each of the processors to execute the programs and implement the functions. Furthermore, in FIG. 1, it is explained that the single memory circuitry 150 stores therein the programs corresponding to each of the processing functions, but it may be possible to arrange a plurality of memory circuitry in a distributed manner and cause the processing circuitry 170 to read a corresponding program from individual memory circuitry.

The term "processor" described in the explanation above indicates, for example, a Central Processing Unit (CPU), a Graphical Processing Unit (GPU), or circuitry, such as Application Specific Integrated Circuit (ASIC), a programmable logic device (for example, a Simple Programmable Logic Device (SPLD), a Complex Programmable Logic Device (CPLD), and a Field Programmable Gate Array (FPGA)), or the like. The processor reads the programs stored in the memory circuitry 150, executes the programs, and implement the functions. Meanwhile, it may be possible to directly incorporate the programs in circuitry of the processor, instead of storing the programs in the memory circuitry 150. In this case, the processor reads the programs incorporated in the circuitry, executes the programs, and implements the functions.

The display control function 171 displays the ultrasound image that is generated by the image generation circuitry 140 on the display 103 or the like. That is, the display control function 171 displays the ultrasound image based on the fourth reflected wave data that is generated by the adaptive reception beamforming unit 114 on the display 103 or the like. The display control function 171 is one example of a display control unit.

Figure 2:
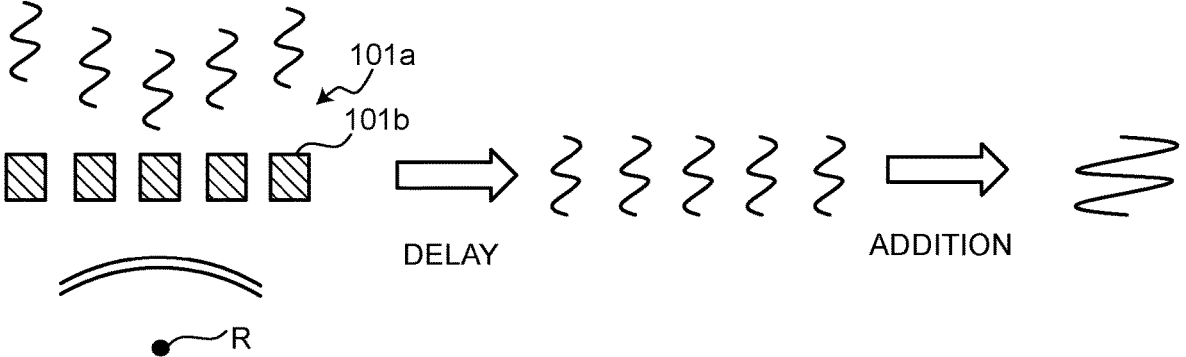
FIG. 2 is a diagram illustrating an example of reception beamforming.

The adaptive reception beamforming will be described below. FIG. 2 is a diagram illustrating an example of reception beamforming. The piezoelectric elements 101b of the array unit 101a receive reflected waves that are reflected by a reflection sound source R that reflects the ultrasound waves transmitted from the piezoelectric elements 101b. The reflected waves are spread in a concentric manner about the reflection sound source R. Therefore, each of the piezoelectric elements 101b that are arrayed receives the reflected wave at a different timing. To cope with this, the ultrasound diagnostic apparatus 100 adds a delay to the reflected wave to adjust the timing. Further, the ultrasound diagnostic apparatus 100 synthesizes the reflected waves to which the delays are added, and acquires enhanced reflected waves from the reflection sound source R. This is a basic processing method called phasing addition or Delay-and-Sum (DAS) in the reception beamforming. The ultrasound diagnostic apparatus 100 performs the adaptive reception beamforming by performing calculation corresponding to the system of the adaptive reception beamforming when adding the delays or synthesizing the reflected waves. The adaptive reception beamforming used in the present application indicates processing in which addition or correction, such as addition of correction delays or calculation and application of a weight from a delayed signal, is performed with respect to phasing delay processing. A large number of prior researches have been made with respect to the adaptive beamforming, and examples of the adaptive beamforming include a Minimum Variance method, a Coherence Factor Imaging method, and a Delay Multiply and Sum (DMAS) method.

Figure 3:
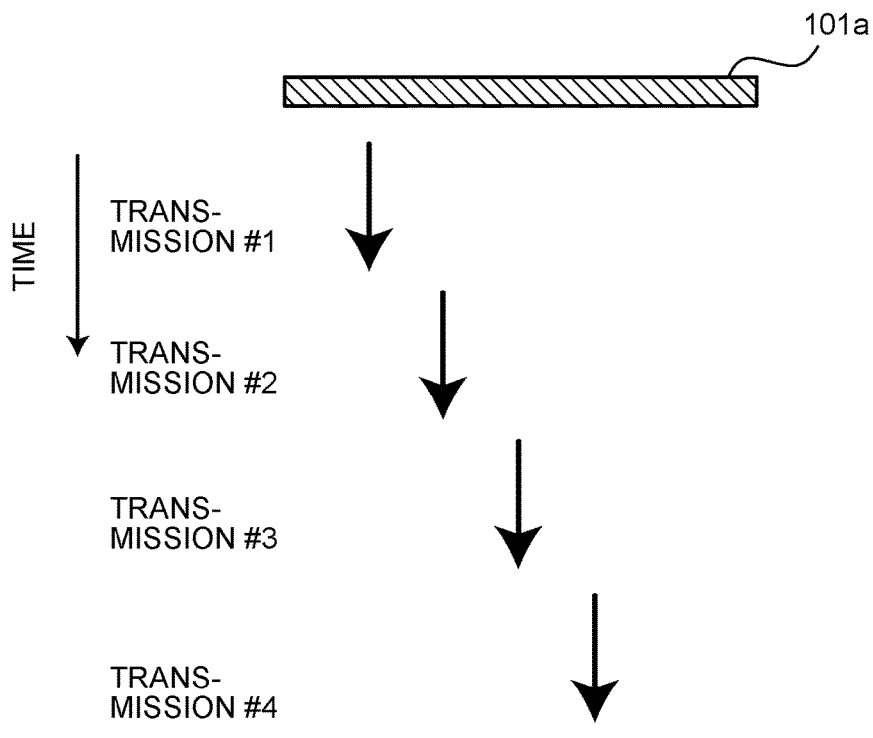
FIG. 3 is a diagram illustrating an example of transmission by transmit aperture synthesis.
Figure 4:
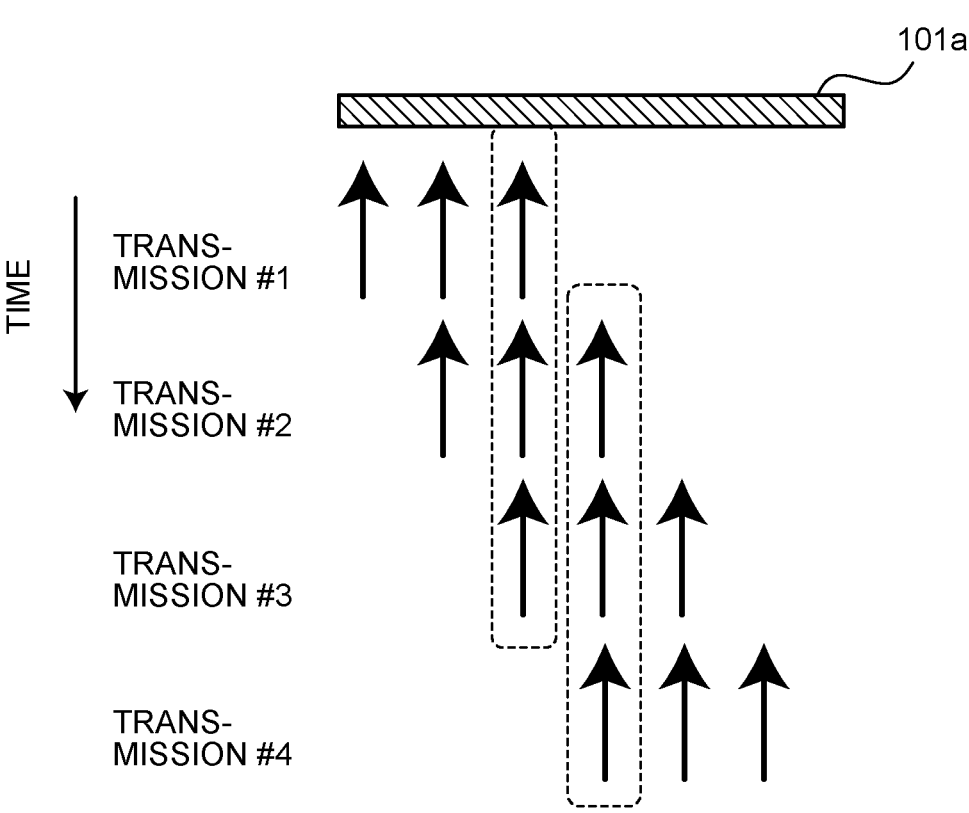
FIG. 4 is a diagram illustrating an example of reception by the transmit aperture synthesis.

Transmission aperture synthesis will be described below. FIG. 3 is a diagram illustrating an example of transmission by the transmit aperture synthesis. FIG. 4 is a diagram illustrating an example of reception by the transmit aperture synthesis. As illustrated in FIG. 3, the array unit 101a transmits ultrasound waves in a plurality of directions at predetermined time intervals, with respect to transmission numbers that indicate respective transmission of the ultrasound waves. A size of the transmit aperture is limited, and therefore, directivity of the formed ultrasound wave is spatially spread. Therefore, even if the ultrasound waves are transmitted in different directions, the ultrasound waves may be reflected by the same reflection sound source R. In this case, in the array unit 101a, the same piezoelectric element 101b receives reflected waves that travel form the same direction upon reflection of the plurality of ultrasound waves that are transmitted in the different directions.

As illustrated in FIG. 4, the array unit 101a performs phasing addition by using the reflected waves of the plurality of ultrasound waves that are transmitted in the different directions, and obtains a reflected signal from a predetermined region. In FIG. 4, as one example, reflected signals in three different directions are generated from the same reflected wave array, by adding different delay amounts.

The ultrasound diagnostic apparatus 100 performs, among different transmission, phasing synthesis of the reflected waves that are received by the same piezoelectric element 101b among the reflected waves of the plurality of ultrasound waves that are transmitted in the different directions. For example, as indicated by dotted frames in FIG. 4, the ultrasound diagnostic apparatus 100 performs phasing addition of the reflected waves corresponding to a transmission number #1, a transmission number #2, and a transmission number #3, obtains reflected signals that are common among the transmission, and further adds the reflected signals among the transmission. Accordingly, the ultrasound diagnostic apparatus 100 improves uniformity of the sound field and a signal-to-noise ratio.

A method of applying the adaptive reception beamforming to the transmit aperture synthesis will be described below.

Figure 5:
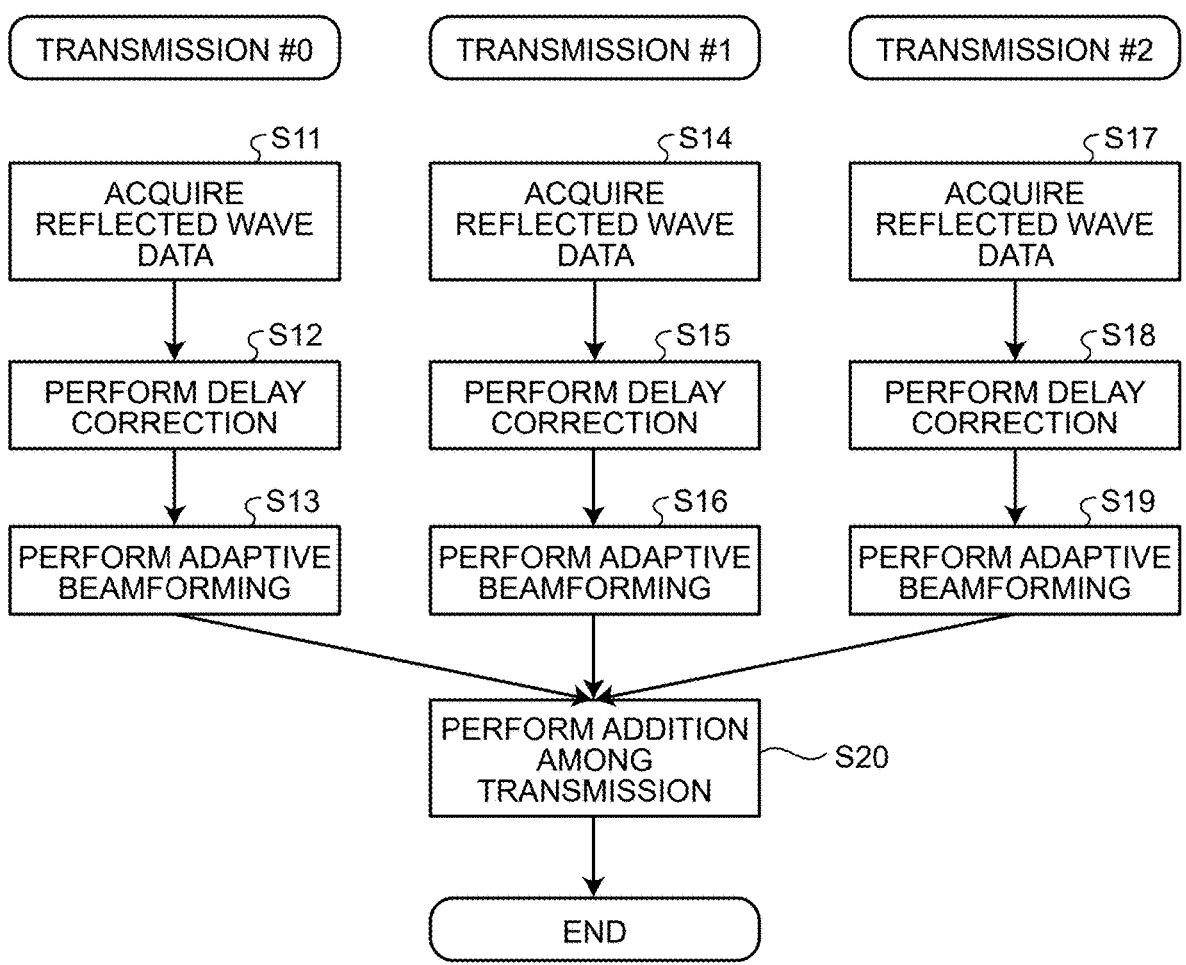
FIG. 5 is a flowchart illustrating an example of a process of applying adaptive reception beamforming to the transmit aperture synthesis.

FIG. 5 is a flowchart illustrating an example of a process of applying the adaptive reception beamforming to the transmit aperture synthesis. Meanwhile, in the flowchart illustrated in FIG. 5, a case is illustrated in which ultrasound waves are transmitted at the transmission number #0 to the transmission number #2, but it is possible to arbitrarily set target transmission numbers.

The ultrasound diagnostic apparatus acquires reflected wave data that indicates a reflected wave received by each of the piezoelectric elements included in the ultrasound probe, with respect to the ultrasound wave transmitted at the transmission number #0 (Step S11).

The ultrasound diagnostic apparatus performs correction for adding a delay to the reflected wave data for each of the piezoelectric elements (Step S12).

The ultrasound diagnostic apparatus performs the adaptive reception beamforming on the reflected wave data to which the delay is added (Step S13).

At Step S14 to Step S16, the ultrasound diagnostic apparatus performs the same processes as those at Step S11 to Step S13, with respect to the reflected wave data corresponding to the ultrasound wave transmitted at the transmission number #1.

At Step S17 to Step S19, the ultrasound diagnostic apparatus performs the same processes as those at Step S11 to Step S13, with respect to the reflected wave data corresponding to the ultrasound wave transmitted at the transmission number #2.

The ultrasound diagnostic apparatus synthesizes the reflected wave data by the addition processing among the transmission of the ultrasound waves (Step S20). That is, the ultrasound diagnostic apparatus performs the transmit aperture synthesis.

Thus, the ultrasound diagnostic apparatus is able to apply the adaptive reception beamforming to the transmit aperture synthesis.

However, in the process illustrated in FIG. 5, the ultrasound diagnostic apparatus performs the adaptive reception beamforming for each transmission of the ultrasound wave, so that a processing load is increased. Further, the ultrasound diagnostic apparatus is operated by a medical worker while the medical worker is viewing an ultrasound image, and therefore needs to ensure real-time performance. To maximize the real-time performance of the ultrasound diagnostic apparatus, it is desirable to update an image at a certain time interval corresponding to a round-trip transmission time of the ultrasound wave, which is needed to scan an image capturing region. However, when the adaptive reception beamforming is performed every time the ultrasound wave is transmitted, and if an increased processing time exceeds the time that is needed to perform ultrasound scanning on the image capturing region, the ultrasound diagnostic apparatus needs to take a countermeasure, such as reduction of an update rate of the ultrasound image, in order to prevent image delay, so that the real-time performance is degraded.

To cope with this, the ultrasound diagnostic apparatus 100 performs an application process of applying the adaptive reception beamforming to the transmit aperture synthesis while reducing the processing load.

Figure 6:
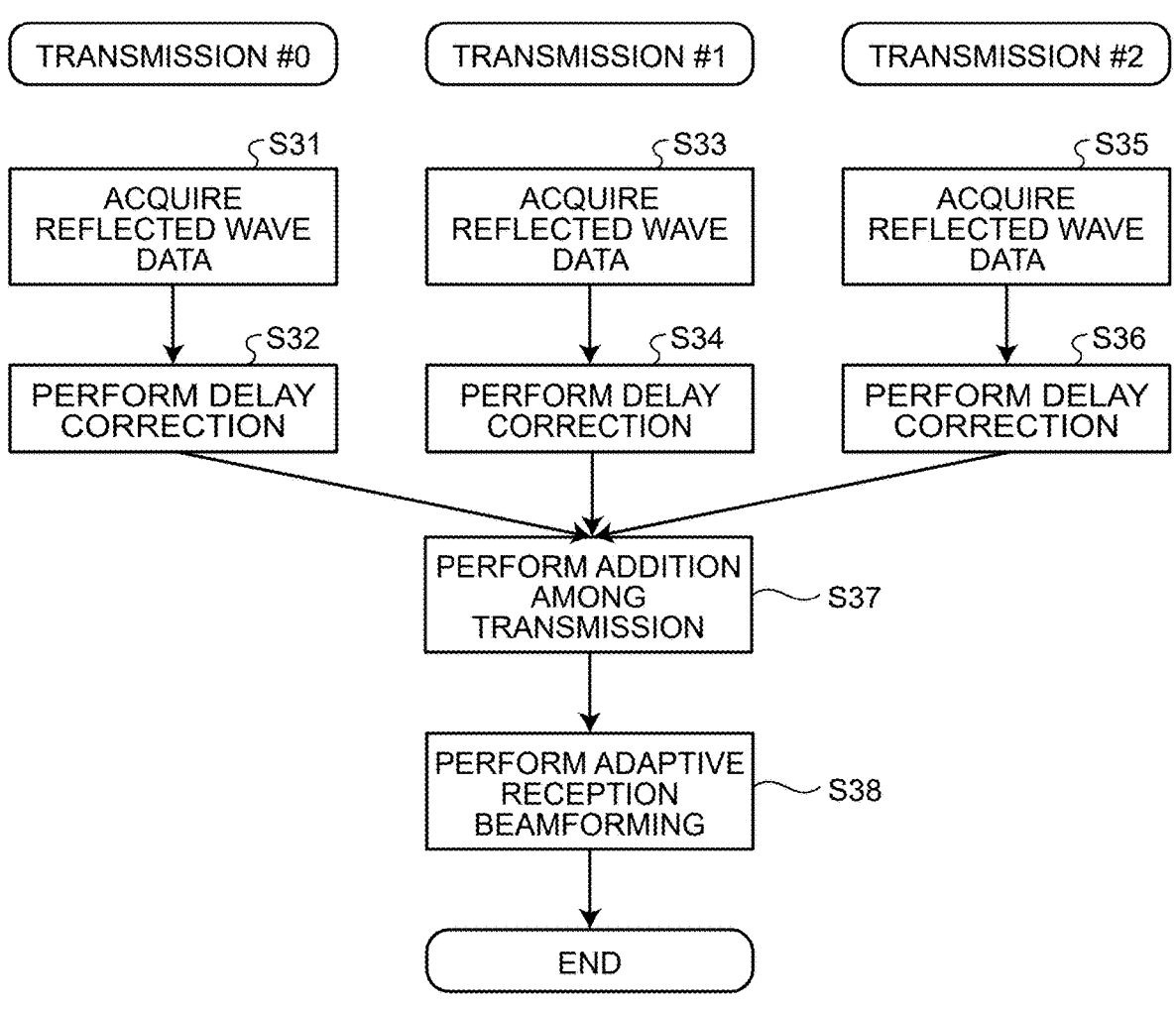
FIG. 6 is a flowchart illustrating an example of an application process performed by the ultrasound diagnostic apparatus according to the present embodiment.

FIG. 6 is a flowchart illustrating an example of the application process performed by the ultrasound diagnostic apparatus 100 according to the present embodiment. The application process is a process of applying the adaptive reception beamforming to the transmit aperture synthesis. Meanwhile, in the application process illustrated in FIG. 6, a case is illustrated in which ultrasound waves are transmitted at the transmission number #0 to the transmission number #2, but it is possible to arbitrarily set target transmission numbers.

The acquisition unit 111 acquires reflected wave data that indicates a reflected wave received by each of the piezoelectric elements 101b included in the ultrasound probe 101, with respect to the ultrasound wave transmitted at the transmission number #0 (Step S31). That is, the acquisition unit 111 acquires the first ultrasound wave data.

The delay correction unit 112 performs correction for adding a delay to the reflected wave data for each of the piezoelectric elements 101b (Step S32). More specifically, the delay correction unit 112 adds a delay corresponding to a transmission path including a forward path from the piezoelectric elements 101b to the reflection sound source R and a backward path from the reflection sound source R to the piezoelectric elements 101b. That is, the delay correction unit 112 generates the second ultrasound wave data.

At Step S33 and Step S34, the ultrasound diagnostic apparatus 100 performs the same processes as those at Step S31 and Step S32, with respect to the reflected wave data corresponding to the ultrasound wave transmitted at the transmission number #1.

At Step S35 and Step S36, the ultrasound diagnostic apparatus 100 performs the same processes as those at Step S31 and Step S32, with respect to the reflected wave data corresponding to the ultrasound wave transmitted at the transmission number #2.

The transmit aperture synthesis unit 113 synthesizes the reflected wave data of the respective piezoelectric elements 101b by the addition processing among the transmission of the ultrasound waves (Step S37). That is, the transmit aperture synthesis unit 113 performs the transmit aperture synthesis for synthesizing the plurality of pieces of second ultrasound data by the addition processing. Accordingly, the transmit aperture synthesis unit 113 generates third ultrasound data.

The adaptive reception beamforming unit 114 performs the adaptive reception beamforming on the synthesized reflected wave data (Step S38). That is, the adaptive reception beamforming unit 114 performs the adaptive reception beamforming of the MV system or the DMAS system on the third ultrasound data, and generates fourth ultrasound data.

Thus, the ultrasound diagnostic apparatus 100 terminates the application process. In the application process illustrated in FIG. 6, the pieces of reflected wave data are synthesized among the transmission of the ultrasound waves and thereafter the adaptive reception beamforming is performed. Therefore, the ultrasound diagnostic apparatus 100 need not perform the adaptive reception beamforming every time the ultrasound wave is transmitted, so that it is possible to reduce the processing load.

As described above, the ultrasound diagnostic apparatus 100 according to the present embodiment transmits ultrasound waves in a plurality of different directions, and upon receiving a plurality of reflected waves, synthesizes the pieces of reflected wave data corresponding to the plurality of reflected waves by the transmit aperture synthesis, and performs the adaptive reception beamforming on the synthesized reflected wave data. With this configuration, the ultrasound diagnostic apparatus 100 is able to reduce the processing load as compared to a case in which the adaptive reception beamforming is performed every time the ultrasound wave is transmitted. Therefore, the ultrasound diagnostic apparatus 100 according to the present embodiment is able to apply the adaptive reception beamforming to the transmit aperture synthesis while reducing the processing load.

Furthermore, in the process illustrated in FIG. 5, the adaptive reception beamforming is performed every time the ultrasound wave is transmitted, so that optimization is performed in accordance with individual transmission. In other words, in the process illustrated in FIG. 5, in the adaptive reception beamforming, optimization is not performed for each transmission of a plurality of ultrasound waves. In contrast, the ultrasound diagnostic apparatus 100 performs the adaptive reception beamforming after performing the transmit aperture synthesis. That is, the ultrasound diagnostic apparatus 100 performs optimization with respect to transmission of a plurality of ultrasound waves. Therefore, the ultrasound diagnostic apparatus 100 is able to improve image quality as compared to the ultrasound image that is generated by performing the transmit aperture synthesis after the adaptive reception beamforming as illustrated in FIG. 5.

First Modification

An ultrasound diagnostic apparatus 100a according to a first modification represents an application example to what is called a Coherence Factor Imaging method to evaluate coherency that indicates a degree of phase match of a reception signal of each of the piezoelectric elements 101b and improve image quality.

Figure 7:
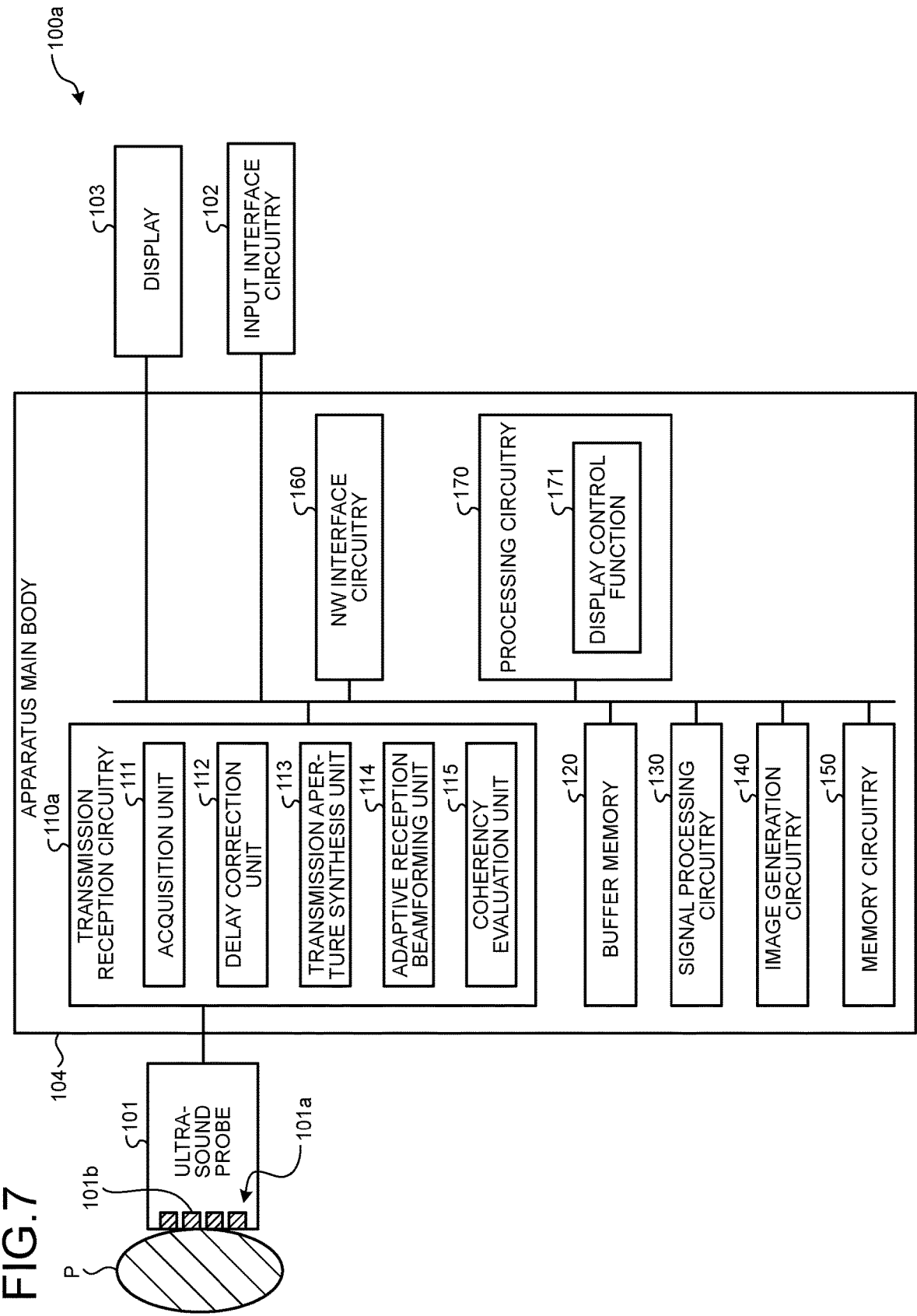
FIG. 7 is a block diagram illustrating an example of a configuration of an ultrasound diagnostic apparatus according to a first modification.

FIG. 7 is a block diagram illustrating an example of a configuration of the ultrasound diagnostic apparatus 100a according to the first modification. Transmission reception circuitry 110a includes a coherency evaluation unit 115.

The coherency evaluation unit 115 calculates a coherency evaluation value that indicates a degree of phase match. More specifically, the coherency evaluation unit 115 calculates the coherency evaluation value with respect to the plurality of pieces of second reflected wave data synthesized by the transmit aperture synthesis unit 113. The coherency evaluation unit 115 is one example of a calculation unit.

Here, the phase of the reflected wave data decreases with a decrease in a distance from a reflection point of the transmitted ultrasound wave to a focal point of transmission of the ultrasound wave. That is, the coherency evaluation value decreases with a decrease in the distance from the reflection point of the transmitted ultrasound wave to the focal point of the transmission of the ultrasound wave. Therefore, a weight of the reflected wave data of the reflected wave that is reflected at a position distant from the focal point is reduced. Thus, the coherency evaluation unit 115 multiplies the fourth reflected wave data that is generated by performing the adaptive reception beamforming by a value that is based on the coherency evaluation value. For example, the coherency evaluation unit 115 multiplies the fourth reflected wave data that is generated by performing the adaptive reception beamforming by the coherency evaluation value. Alternatively, the coherency evaluation unit 115 need not always multiply the coherency evaluation value, but may multiply the fourth reflected wave data by a weight corresponding to the evaluation value. Further, by multiplying the fourth reflected wave data subjected to the adaptive reception beamforming by the coherency evaluation value, the coherency evaluation unit 115 is able to improve the image quality.

Figure 8:
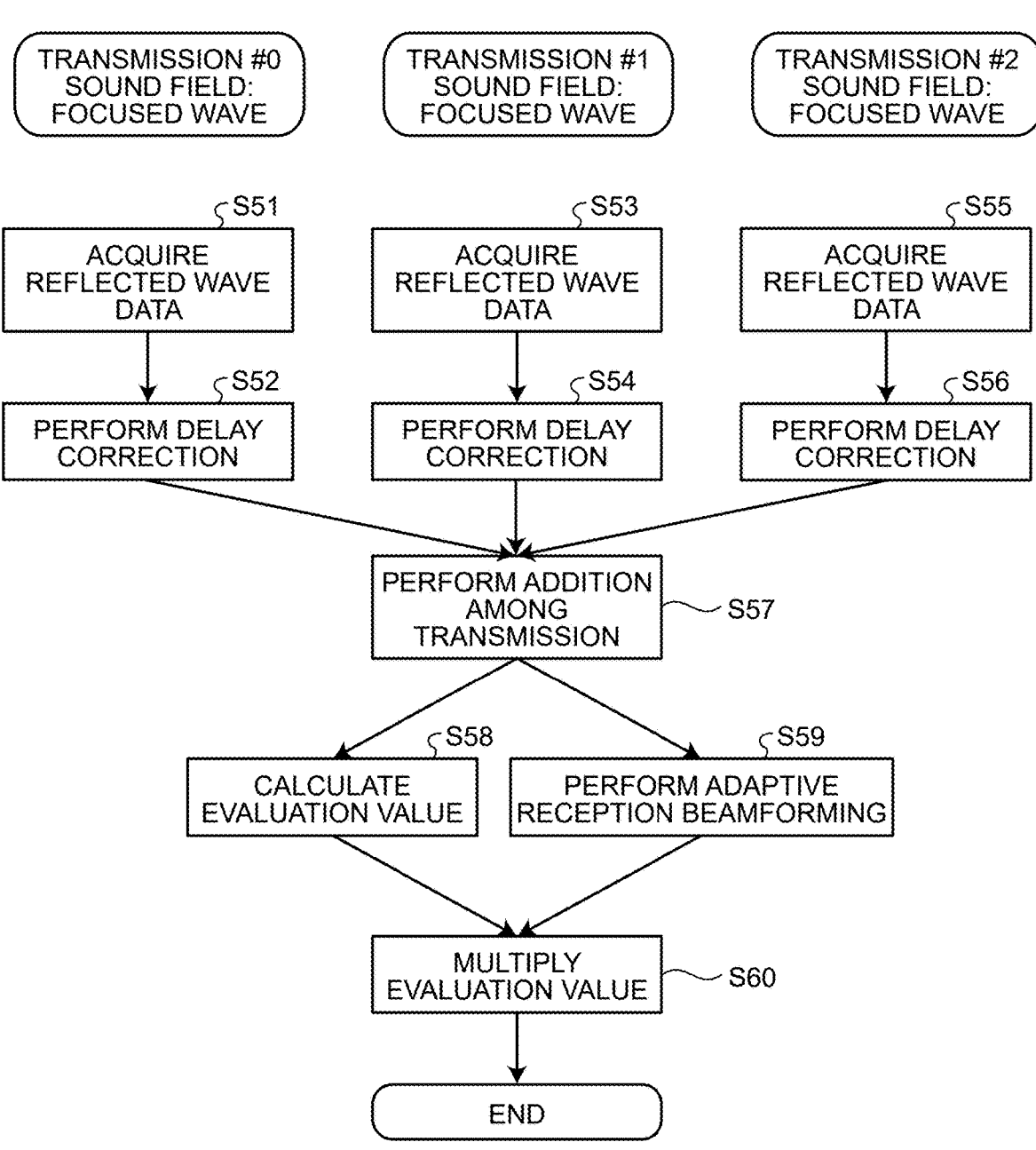
FIG. 8 is a flowchart illustrating an example of an application process performed by the ultrasound diagnostic apparatus according to the first modification.

FIG. 8 is a flowchart illustrating an example of the application process performed by the ultrasound diagnostic apparatus 100a according to the first modification. Meanwhile, in the application process illustrated in FIG. 8, a case is illustrated in which ultrasound waves are transmitted at the transmission number #0 to the transmission number #2, but it is possible to arbitrarily set target transmission numbers.

The acquisition unit 111 acquires the reflected wave data indicating the reflected wave that is received by each of the piezoelectric elements 101b included in the ultrasound probe 101, with respect to the ultrasound wave transmitted at the transmission number #1 (Step S51). That is, the acquisition unit 111 acquires the first ultrasound wave data.

The delay correction unit 112 performs a correction of adding a delay to the reflected wave data of each of the piezoelectric elements 101b (Step S52). More specifically, the delay correction unit 112 adds a delay corresponding to a transmission path including a forward path from the piezoelectric elements 101b to the reflection sound source R and a backward path from the reflection sound source R to the piezoelectric elements 101b. That is, the delay correction unit 112 generates the second ultrasound wave data.

At Step S53 and Step S54, the ultrasound diagnostic apparatus 100a performs the same processes as those at Step S51 and Step S52, with respect to the reflected wave data corresponding to the ultrasound wave transmitted at the transmission number #1.

At Step S55 and Step S56, the ultrasound diagnostic apparatus 100a performs the same processes as those at Step S51 and Step S52, with respect to the reflected wave data corresponding to the ultrasound wave transmitted at the transmission number #2.

The transmit aperture synthesis unit 113 synthesizes the reflected wave data by the addition processing among the transmission of the ultrasound waves (Step S57). That is, the transmit aperture synthesis unit 113 performs the transmit aperture synthesis for synthesizing the plurality of pieces of second ultrasound data by the addition processing. Accordingly, the transmit aperture synthesis unit 113 generates the third ultrasound data.

The coherency evaluation unit 115 calculates a coherency evaluation value that indicates a degree of phase match of the reflected wave data, with respect to the pieces of reflected wave data that are added among the transmission at Step S57 (Step S58). That is, the coherency evaluation unit 115 calculates the coherency evaluation value with respect to the plurality of pieces of second reflected wave data.

The adaptive reception beamforming unit 114 performs the adaptive reception beamforming on the third reflected wave data synthesized by the transmit aperture synthesis (Step S59). That is, the adaptive reception beamforming unit 114 performs the adaptive reception beamforming of the MV system or the MDAS system on the third ultrasound data, and generates the fourth ultrasound data.

The coherency evaluation unit 115 multiplies the reflected wave data that is subjected to the adaptive reception beamforming by the coherency evaluation value (Step S60). That is, the coherency evaluation unit 115 generates fifth ultrasound wave data by multiplying the fourth ultrasound data by the coherency evaluation value. Further, the coherency evaluation unit 115 stores the fifth ultrasound wave data, as the ultrasound wave data, in the buffer memory 120.

Thus, the ultrasound diagnostic apparatus 100a according to the first modification terminates the application process. Meanwhile, in the present modification, the adaptive reception beamforming is performed in addition to coherency evaluation, but it is possible to arbitrarily determine whether to use the adaptive reception beamforming, that is, whether to use the conventional beamforming of adding the plurality of pieces of second reflected wave data.

As described above, the ultrasound diagnostic apparatus 100a according to the first modification calculates the coherency evaluation value from the plurality of pieces of second ultrasound data. Further, the ultrasound diagnostic apparatus 100a multiples the fourth ultrasound data by a certain value corresponding to the evaluation value. Here, the coherency evaluation value decreases as the ultrasound wave that is a basis of the target reflected wave data is transmitted to a more distant position from the focal point. Therefore, by multiplying the fourth ultrasound data by a value corresponding to the evaluation value, the ultrasound diagnostic apparatus 100a is able to improve the image quality of the ultrasound image.

Second Modification

A second modification is applied to Tissue Harmonic Imaging (THI) for visualizing a harmonic component that is generated by a non-linear phenomenon of ultrasound transmission in a biological body.

Figure 9:
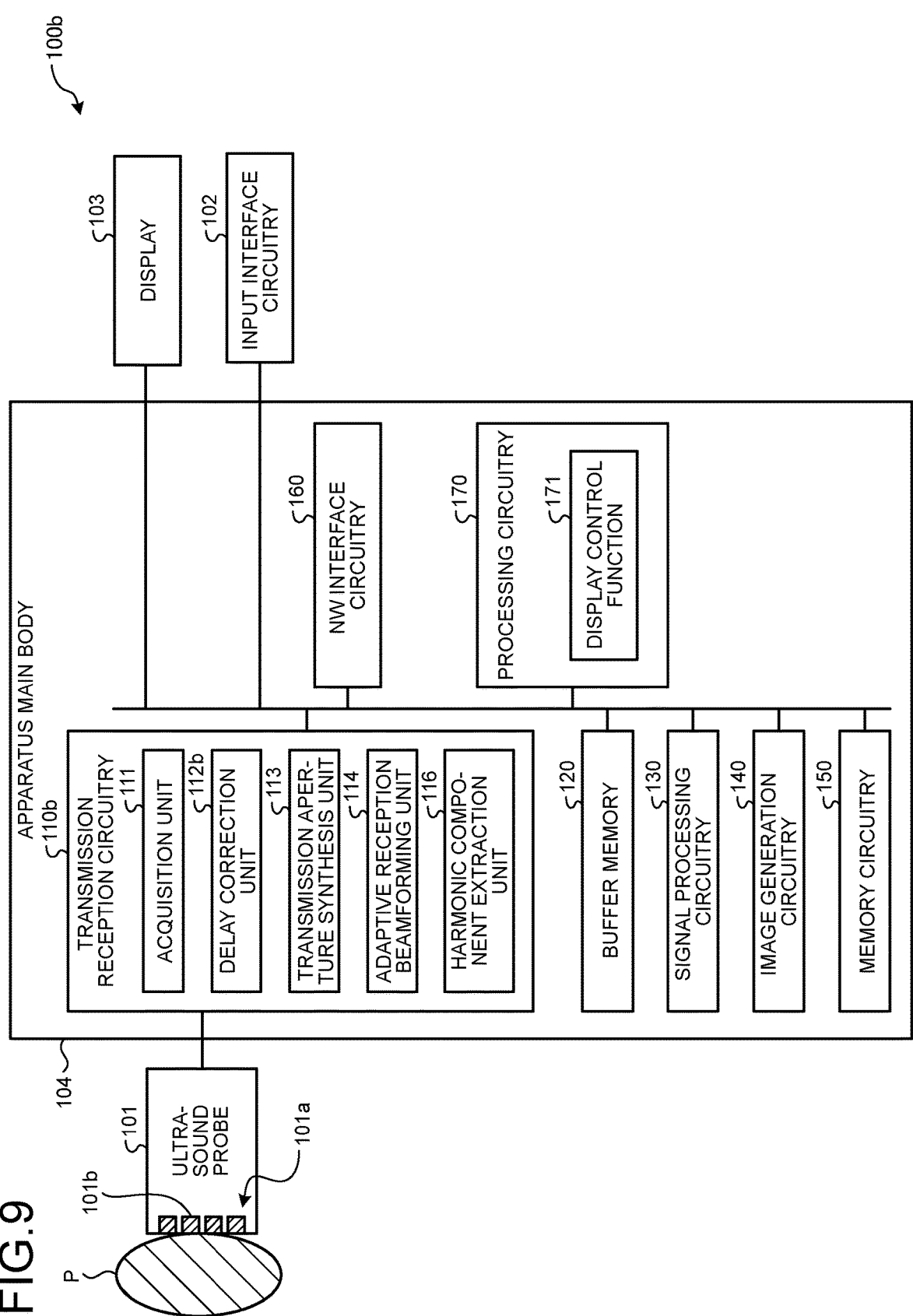
FIG. 9 is a block diagram illustrating an example of a configuration of an ultrasound diagnostic apparatus according to a second modification.

FIG. 9 is a block diagram illustrating an example of a configuration of an ultrasound diagnostic apparatus 100b according to the second modification. Transmission reception circuitry 110b includes a harmonic component extraction unit 116.

The transmission reception circuitry 110b causes, in transmission beamforming, the ultrasound probe 101 to transmit ultrasound waves with different phases. For example, the transmission reception circuitry 110b modulates the phase by 180 degrees every time the ultrasound wave is transmitted in the transmission beamforming for transmitting a converged wave in which the ultrasound waves are converged. Further, the transmission reception circuitry 110b transmits the ultrasound wave that is modulated by 180 degrees. Furthermore, the transmission reception circuitry 110b repeatedly performs phase modulation and transmission of the ultrasound wave in the transmission beamforming. Meanwhile, the transmission reception circuitry 110b need not always modulate the phase by 180 degrees, but may modulate the phase by a different angle.

Furthermore, the transmission reception circuitry 110b may modulate amplitude and perform transmission.

The harmonic component extraction unit 116 extracts a harmonic component from a reflected wave signal indicated by the reflected wave data. For example, the harmonic component extraction unit 116 extracts the harmonic component from the first reflected wave data that is acquired by the acquisition unit 111. The harmonic component extraction unit 116 is one example of an extraction unit.

More specifically, the harmonic component extraction unit 116 extracts an even-ordered harmonic component by adding a plurality of pieces of first reflected wave data that are generated by chronologically transmitting and receiving ultrasound waves with different phases and in different transmission directions. More specifically, the harmonic component extraction unit 116 extracts the harmonic component based on one piece of the first reflected wave data that is generated by chronologically transmitting and receiving certain ultrasound waves and based on another piece of the first reflected wave data that is generated by chronologically transmitting and receiving phase-modulated ultrasound waves that are obtained by modulating the phase of the certain ultrasound waves.

For example, the harmonic component extraction unit 116 extracts the harmonic component based on one piece of the first reflected wave data of the reflected wave corresponding to a certain ultrasound wave that is transmitted with the phase of 0 degree and another piece of the first reflected wave data of the reflected wave corresponding to a phase-modulated ultrasound wave that is transmitted with a 180-degree modulated phase. That is, the harmonic component extraction unit 116 extracts the even-ordered harmonic component by adding pieces of the first reflected wave data with different phases. When the even-ordered harmonic component is extracted, the harmonic component extraction unit 116 generates the fifth reflected wave data that is the reflected wave data indicating the harmonic component that is extracted from the reflected wave.

A delay correction unit 112b performs a correction of adding a delay to the fifth reflected wave data. That is, the delay correction unit 112b performs the phasing addition processing on the harmonic component of the reflected wave that is extracted by the harmonic component extraction unit 116. More specifically, the delay correction unit 112b generates the second ultrasound wave data by adding, to the fifth reflected wave data, a delay corresponding to a transmission path including a forward path from the piezoelectric elements 101b to the reflection sound source R and a backward path from the reflection sound source R to the piezoelectric elements 101b.

Figure 10:
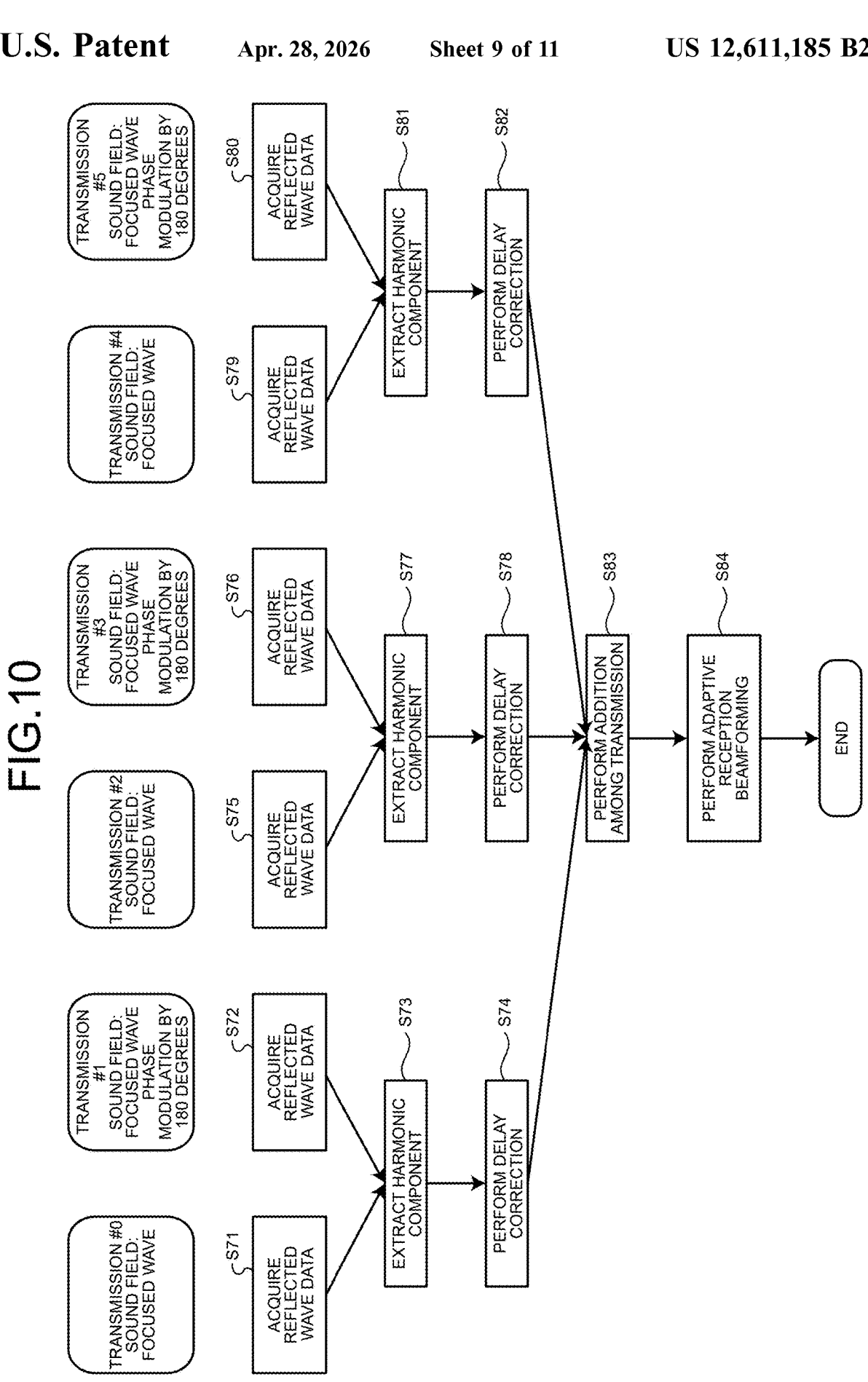
FIG. 10 is a flowchart illustrating an example of an application process performed by the ultrasound diagnostic apparatus according to the second modification.

FIG. 10 is a flowchart illustrating an example of an application process that is performed by the ultrasound diagnostic apparatus 100b according to the second modification. Meanwhile, in the application process illustrated in FIG. 10, a case is illustrated in which ultrasound waves are transmitted at the transmission number #0 to the transmission number #5, but it is possible to arbitrarily set target transmission numbers.

At the transmission number #0, the ultrasound probe 101 converges ultrasound waves by the transmission beamforming and transmits the converged wave. The acquisition unit 111 acquires the reflected wave data indicating the reflected wave that is received by each of the piezoelectric elements 101*b* included in the ultrasound probe 101, with respect to the ultrasound wave transmitted at the transmission number #0 (Step S71). That is, the acquisition unit 111 acquires the first ultrasound wave data.

At the transmission number #1, the ultrasound probe 101 modulates the phase by 180 degrees with respect to the transmission number #0, converges the ultrasound waves by the transmission beamforming, and transmits the converged wave. The acquisition unit 111 acquires the reflected wave data that indicates the reflected wave that is received by each of the piezoelectric elements 101*b* included in the ultrasound probe 101 with respect to the ultrasound wave transmitted at the transmission number #1 (Step S72). That is, the acquisition unit 111 acquires the first ultrasound wave data.

The harmonic component extraction unit 116 extracts the harmonic component by adding one piece of the first reflected wave data and another piece of the first reflected wave data indicating the reflected wave corresponding to a phase-modulated ultrasound wave that has a phase 180 degrees modulated from the ultrasound wave corresponding to the one piece of the first reflected wave data (Step S73). That is, the harmonic component extraction unit 116 extracts the harmonic component by adding the first reflected wave data that is acquired at Step S71 and the first reflected wave data that is acquired at Step S72. Accordingly, the harmonic component extraction unit 116 generates the fifth reflected wave data that indicates the harmonic component extracted from the reflected wave.

The delay correction unit 112*b* performs a correction of adding a delay to the reflected wave data of the extracted harmonic component (Step S74). More specifically, the delay correction unit 112*b* adds a delay corresponding to a transmission path including a forward path from the piezoelectric elements 101*b* to the reflection sound source R and a backward path from the reflection sound source R to the piezoelectric elements 101*b*. That is, the delay correction unit 112*b* generates the second ultrasound wave data by adding the delay to the fifth reflected wave data.

Further, at Step S75 to Step S78, the ultrasound diagnostic apparatus 100*b* performs the same processes as those at Step S71 to Step S74.

Furthermore, at Step S79 to Step S82, the ultrasound diagnostic apparatus 100*b* performs the same processes as those at Step S71 to Step S74.

The transmit aperture synthesis unit 113 synthesizes the reflected wave data by the addition processing among the transmission of the ultrasound waves (Step S83). That is, the transmit aperture synthesis unit 113 performs the transmit aperture synthesis for synthesizing the plurality of pieces of second ultrasound data by the addition processing. Accordingly, the transmit aperture synthesis unit 113 generates the third ultrasound data.

The adaptive reception beamforming unit 114 performs the adaptive reception beamforming on the synthesized reflected wave data (Step S84). For example, the adaptive reception beamforming unit 114 performs the adaptive reception beamforming of the MV system or the DMAS system on the third ultrasound data, and generates the fourth ultrasound data.

Thus, the ultrasound diagnostic apparatus 100*b* terminates the application process.

As described above, the ultrasound diagnostic apparatus 100*b* according to the second modification performs the transmit aperture synthesis and the adaptive reception beamforming on the harmonic component extracted from the first reflected wave data. In this manner, the ultrasound diagnostic apparatus 100*b* is able to perform the transmit aperture synthesis and the adaptive reception beamforming on the tissue harmonic imaging of visualizing the harmonic component that is generated by a non-linear phenomenon of ultrasound transmission in a biological body.

Third Modification

In a third modification, the ultrasound probe 101 transmits a ultrasound wave by a plane wave or a spherical diffused wave. Further, an ultrasound diagnostic apparatus 100*c* applies the adaptive reception beamforming to the transmit aperture synthesis by using a reflected wave of the ultrasound wave that is transmitted by a plane wave or a spherical diffused wave.

Figure 11:
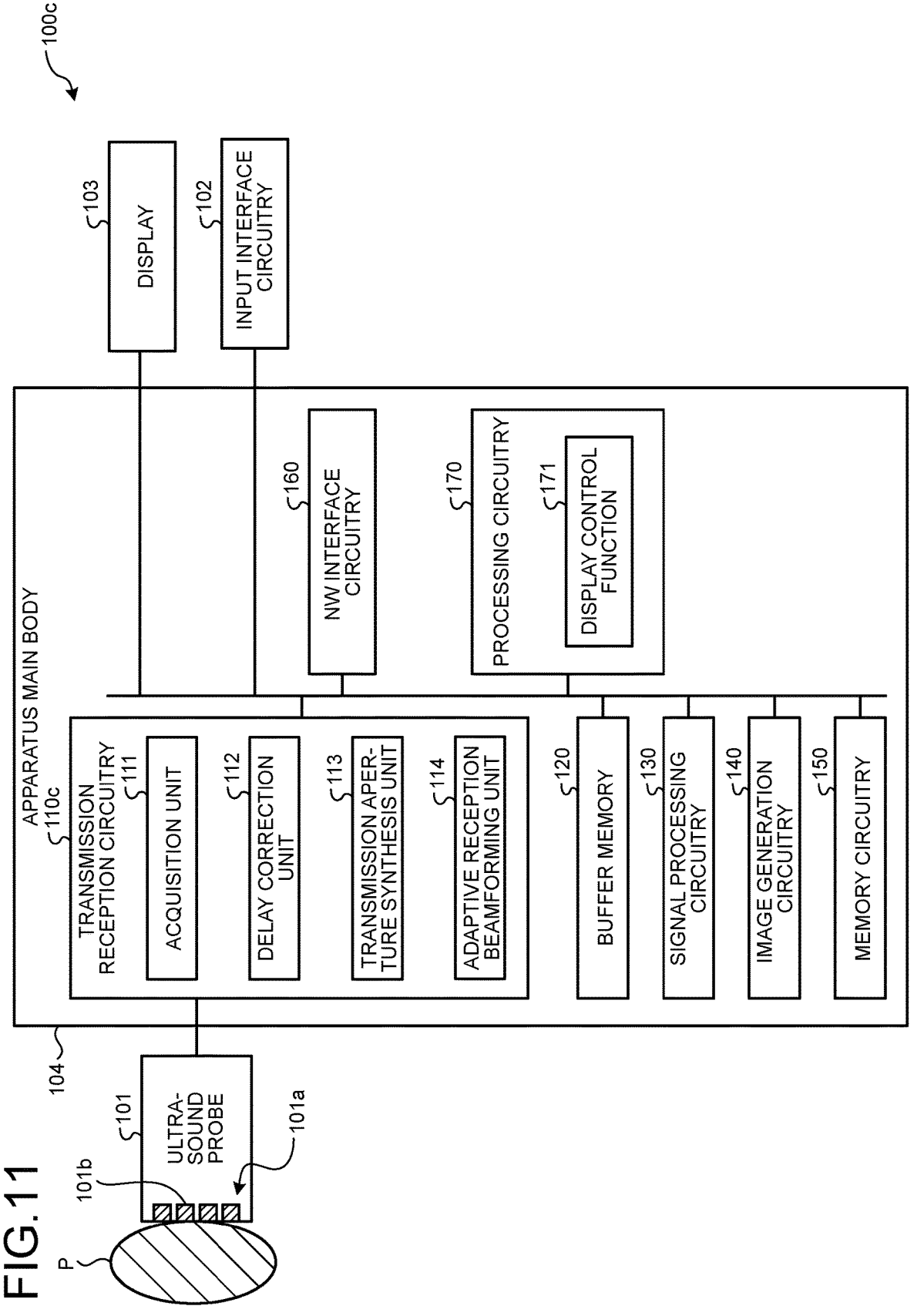
FIG. 11 is a block diagram illustrating an example of a configuration of an ultrasound diagnostic apparatus according to a third modification.

FIG. 11 is a block diagram illustrating an example of a configuration of the ultrasound diagnostic apparatus 100*c* according to the third modification.

More specifically, the piezoelectric elements 101*b* of the array unit 101*a* included in the ultrasound probe 101 transmit ultrasound waves by plane waves or spherical diffused waves while changing a deflection angle. For example, the ultrasound probe 101 transmits the ultrasound wave by a plane wave or a spherical diffused wave while changing the deflection angle by 15 degrees each time. In other words, transmission reception circuitry 110*c* causes the ultrasound probe 101 to transmit the ultrasound wave by a plane wave or a spherical diffused wave while changing the deflection angle by 15 degrees each time.

Further, the piezoelectric elements 101*b* of the array unit 101*a* included in the ultrasound probe 101 receive reflected waves corresponding to the ultrasound wave transmitted by a plane wave or a spherical diffused wave. That is, the acquisition unit 111 acquires the first reflected wave data indicating the reflected wave corresponding to the ultrasound wave that is the plane wave or the spherical diffused wave.

Figure 12:
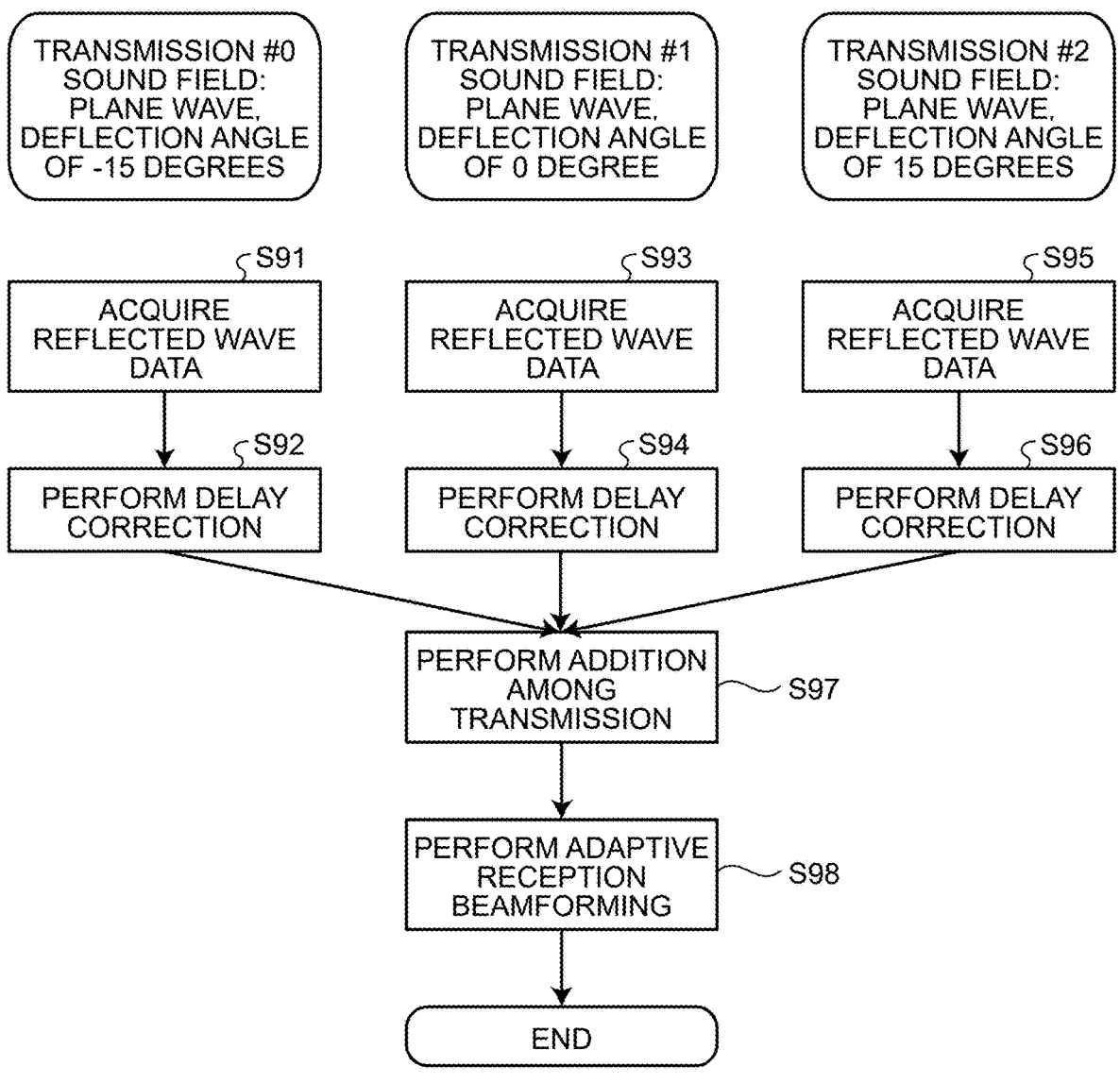
FIG. 12 is a flowchart illustrating an example of an application process performed by the ultrasound diagnostic apparatus according to the third modification.

FIG. 12 is a flowchart illustrating an example of the application process performed by the ultrasound diagnostic apparatus 100*c* according to the third modification. Meanwhile, in the application process illustrated in FIG. 12, a case is illustrated in which ultrasound waves are transmitted at the transmission number #0 to the transmission number #2, but it is possible to arbitrarily set target transmission numbers.

At the transmission number #0, the ultrasound probe 101 transmits an ultrasound wave with the deflection angle of −15 degrees by a plane wave. The acquisition unit 111 acquires the reflected wave data indicating the reflected wave that is received by each of the piezoelectric elements 101*b* included in the ultrasound probe 101, with respect to the ultrasound wave transmitted at the transmission number #0 (Step S91). That is, the acquisition unit 111 acquires the first ultrasound wave data.

The delay correction unit 112 performs a correction of adding a delay to the reflected wave data of each of the piezoelectric elements 101*b* (Step S92). More specifically, the delay correction unit 112 adds a delay corresponding to a transmission path including a forward path from the piezoelectric elements 101*b* to the reflection sound source R and a backward path from the reflection sound source R to the piezoelectric elements 101b. That is, the delay correction unit 112 generates the second ultrasound wave data.

At the transmission number #1, the ultrasound probe 101 transmits the ultrasound wave with the deflection angle of zero degree by a plane wave. At Step S93 and Step S94, the ultrasound diagnostic apparatus 100c performs the same processes as those at Step S91 and Step S92.

The ultrasound probe 101 transmits the ultrasound wave with the deflection angle of zero degree by a plane wave at the transmission number #2. At Step S95 and Step S96, the ultrasound diagnostic apparatus 100c performs the same processes as those at Step S91 and Step S92.

The transmit aperture synthesis unit 113 synthesizes the reflected wave data by the addition processing among the transmission of the ultrasound waves (Step S97). That is, the transmit aperture synthesis unit 113 performs the transmit aperture synthesis for synthesizing the plurality of pieces of second ultrasound data by the addition processing. Accordingly, the transmit aperture synthesis unit 113 generates the third ultrasound data.

The adaptive reception beamforming unit 114 performs the adaptive reception beamforming on the synthesized reflected wave data (Step S98). That is, the adaptive reception beamforming unit 114 performs the adaptive reception beamforming of the MV system or the MDAS system on the third ultrasound data, and generates the fourth ultrasound data.

Thus, the ultrasound diagnostic apparatus 100c terminates the application process.

As described above, the ultrasound diagnostic apparatus 100c according to the third modification is able to perform the transmit aperture synthesis and the adaptive reception beamforming on the reflected wave data that indicates the reflected wave corresponding to the ultrasound wave that is transmitted by a plane wave or a spherical diffused wave.

Fourth Modification

In the present embodiment, each of the transmission reception circuitry 110, 110a, 110b, and 110c includes the acquisition unit 111, the delay correction unit 112, 112b, the transmit aperture synthesis unit 113, the adaptive reception beamforming unit 114, and the coherency evaluation unit 115. That is, it is explained that the acquisition unit 111, the delay correction units 112, 112b, the transmit aperture synthesis unit 113, the adaptive reception beamforming unit 114, and the coherency evaluation unit 115 are implemented by hardware. However, all or a part of the acquisition unit 111, the delay correction units 112, 112b, the transmit aperture synthesis unit 113, the adaptive reception beamforming unit 114, and the coherency evaluation unit 115 may be implemented by a program. That is, the processing circuitry 170 may implement all or a part of functions of the acquisition unit 111, the delay correction units 112, 112b, the transmit aperture synthesis unit 113, the adaptive reception beamforming unit 114, and the coherency evaluation unit 115 by executing a program.

Fifth Modification

In the present embodiment, it is explained that the apparatus main body 104 includes the acquisition unit 111, the delay correction units 112, 112b, the transmit aperture synthesis unit 113, the adaptive reception beamforming unit 114, and the coherency evaluation unit 115. That is, it is explained that the apparatus main body 104 includes the ultrasound reception apparatus. However, all or a part of the acquisition unit 111, the delay correction units 112, 112b, the transmit aperture synthesis unit 113, the adaptive reception beamforming unit 114, and the coherency evaluation unit 115 need not be included in the apparatus main body 104, and may be included in the ultrasound probe 101. That is, the ultrasound probe 101 may include the ultrasound reception apparatus.

According to at least one of the embodiments and the like as described above, it is possible to apply the adaptive reception beamforming to the transmit aperture synthesis while reducing a processing load.

In relation to the embodiments as described above, following notes are disclosed as one of selective features of the present invention.

Note. 1

An ultrasound reception apparatus including:

an acquisition unit that acquires first reflected wave data for each channel, the first reflected wave data being generated by chronologically transmitting and receiving ultrasound waves in different transmission directions;

a phasing addition processing unit that performs phasing addition processing corresponding to a transmission path for each channel with respect to each piece of the first reflected wave data, and generates second reflected wave data;

a transmit aperture synthesis unit that performs addition processing with respect to a plurality of transmission directions by using the second reflected wave data for each channel, and generates third reflected wave data subjected to transmit aperture synthesis; and an adaptive reception beamforming unit that performs adaptive reception beamforming on the third reflected wave data.

Note. 2

The ultrasound reception apparatus may further include a calculation unit that calculates a coherency evaluation value with respect to a plurality of pieces of the second reflected wave data synthesized by the transmit aperture synthesis unit.

Note. 3

The calculation unit may multiply fourth reflected wave data that is generated by performing the adaptive reception beamforming by a value that is based on the evaluation value.

Note. 4

The ultrasound reception apparatus may further include an extraction unit that extracts a harmonic component from the first reflected wave data, and the phasing addition processing unit may perform the phasing addition processing on the harmonic component that is extracted by the extraction unit.

Note. 5

The extraction unit may extract the harmonic component based on one piece of the first reflected wave data that is generated by chronologically transmitting and receiving certain ultrasound waves and based on another piece of the first reflected wave data that is generated by chronologically transmitting and receiving phase-modulated ultrasound waves that are obtained by modulating a phase of the certain ultrasound waves.

Note. 6

The acquisition unit may acquire the first reflected wave data corresponding to an ultrasound wave that is one of a plane wave and a spherical diffused wave.

Note. 7

The adaptive reception beamforming unit may perform the adaptive reception beamforming of a Minimum Variance system.

Note. 8

The adaptive reception beamforming unit may perform the adaptive reception beamforming of a Delay Multiply and Sum system.

Note. 9

The ultrasound reception apparatus may further include a display control unit that displays an ultrasound image that is based on fourth reflected wave data that is generated by performing the adaptive reception beamforming.

Note. 10

An ultrasound wave reception method including:

acquiring first reflected wave data for each channel, the first reflected wave data being generated by chronologically transmitting and receiving ultrasound waves in different transmission directions;

generating second reflected wave data by performing phasing addition processing corresponding to a transmission path for each channel with respect to each piece of the first reflected wave data;

generating third reflected wave data subjected to transmit aperture synthesis by performing addition processing on a plurality of transmission directions by using the second reflected wave data for each channel; and performing adaptive reception beamforming on the third reflected wave data.

Note. 11

The transmit aperture synthesis may be processing of synthesizing, for each channel, reflected waves that are obtained by reflecting the ultrasound waves that are transmitted in different directions at a plurality of timings.

Note. 12

The phasing addition processing may be processing of adding, to the first reflected wave data, a delay corresponding to a transmission path including a forward path until reflection of ultrasound waves transmitted from the piezoelectric elements and a backward path to the piezoelectric elements after the reflection of the transmitted ultrasound waves.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound reception apparatus applying adaptive reception beamforming to synthesis processing, the apparatus comprising:

signal processing circuitry configured to:

sequentially acquire a plurality of pieces of first reflected wave data for each channel, the plurality of pieces of first reflected wave data indicating reflected waves corresponding to ultrasound waves transmitted at a plurality of timings, respectively;

perform delay correction processing corresponding to a transmission path of the reflected waves with respect to the plurality of pieces of first reflected wave data, thereby generating, for each channel, a plurality of pieces of second reflected wave data for the plurality of timings;

perform synthesis processing with respect to the plurality of pieces of second reflected wave data, thereby generating one piece of third reflected wave data; and perform adaptive reception beamforming on the one piece of third reflected wave data, thereby acquiring one piece of fourth reflected wave data.

2. The ultrasound reception apparatus according to claim 1, wherein the signal processing circuitry is further configured to calculate an evaluation value for coherency between the plurality of pieces of the second reflected wave data.

3. The ultrasound reception apparatus according to claim 2, wherein the signal processing circuitry is configured to multiply the one piece of fourth reflected wave data that is generated by performing the adaptive reception beamforming by a value that is based on the evaluation value, thereby acquiring fifth reflected wave data.

4. The ultrasound reception apparatus according to claim 1, wherein the signal processing circuitry is further configured to extract a harmonic component from the plurality of pieces of first reflected wave data, and the signal processing circuitry is configured to generate, for each channel, the plurality of pieces of second reflected wave data by performing the delay correction processing on the harmonic component extracted.

5. The ultrasound reception apparatus according to claim 4, wherein the signal processing circuitry is configured to extract the harmonic by adding the plurality of pieces of first reflected wave data indicating the reflected waves corresponding to the ultrasound waves transmitted at the plurality of timings, respectively and another piece of the first reflected wave data indicating a reflected wave corresponding to a phase-modulated ultrasound wave that is obtained by modulating a phase of one of the ultrasound waves.

6. The ultrasound reception apparatus according to claim 1, wherein the signal processing circuitry is configured to acquire the plurality of pieces of first reflected wave data corresponding to the ultrasound waves that are one of a plane wave and a spherical diffused wave.

7. The ultrasound reception apparatus according to claim 1, wherein the adaptive reception beamforming performed by the signal processing circuitry is Minimum Variance beamforming.

8. The ultrasound reception apparatus according to claim 1, wherein the adaptive reception beamforming performed by the signal processing circuitry is Delay Multiply and Sum beamforming.

9. An ultrasound wave reception method applying adaptive reception beamforming to synthesis processing, the method comprising:

sequentially acquiring a plurality of pieces of first reflected wave data for each channel, the plurality of pieces of first reflected wave data indicating reflected waves corresponding to ultrasound waves transmitted at a plurality of timings, respectively;

generating, for each channel, a plurality of pieces of second reflected wave data for the plurality of timings by performing delay correction processing corresponding to a transmission path of the reflected waves with respect to the plurality of pieces of first reflected wave data;

generating one piece of third reflected wave data by performing synthesis processing with respect to the plurality of pieces of second reflected wave data; and acquiring one piece of fourth reflected wave data by performing adaptive reception beamforming on the one piece of third reflected wave data.

* * * * *